United States Patent [19]

Weiler et al.

[11] Patent Number: 4,951,659
[45] Date of Patent: Aug. 28, 1990

[54] NEBULIZER WITH COOPERATING DISENGAGEABLE ON-LINE HEATER

[75] Inventors: Gerhard H. Weiler, South Barrington; Henry Komendowski, Des Plaines, both of Ill.

[73] Assignee: Automatic Liquid Packaging, Inc., Woodstock, Ill.

[21] Appl. No.: 267,071

[22] Filed: Nov. 4, 1988

[51] Int. Cl.[5] .................... A61M 11/02; A61M 16/10

[52] U.S. Cl. .......................... 128/200.18; 128/200.21; 128/203.16; 128/203.17; 128/203.26; 128/203.27

[58] Field of Search ...................... 128/200.14, 200.18, 128/200.21, 203.12, 203.16, 203.17, 203.25, 203.26, 203.27, 204.17

[56] References Cited

U.S. PATENT DOCUMENTS

| | | | |
|---|---|---|---|
| 2,116,328 | 5/1938 | Silten | 128/203.16 |
| 3,353,536 | 11/1967 | Bird et al. | 128/200.18 |
| 3,572,660 | 3/1971 | Mahon | 128/200.18 |
| 3,580,249 | 5/1971 | Takaoka | 128/200.14 |
| 3,695,267 | 10/1972 | Hirtz et al. | 128/203.17 |
| 3,771,721 | 11/1973 | Van Amerongen | 128/200.18 |
| 3,915,386 | 10/1975 | Vora | 128/200.18 |
| 4,190,046 | 2/1980 | Virag | 128/204.17 |
| 4,195,004 | 3/1980 | Miller | 128/200.21 |
| 4,243,396 | 1/1981 | Cronenberg | 128/203.16 |
| 4,267,974 | 5/1981 | Kienholz et al. | 128/203.25 |
| 4,369,777 | 1/1983 | Lwoff et al. | 128/200.14 |
| 4,427,004 | 1/1984 | Miller | 128/203.27 |
| 4,461,425 | 7/1984 | Miller | 128/203.27 |
| 4,589,409 | 5/1986 | Chatburn et al. | 128/203.26 |
| 4,620,670 | 11/1986 | Hughes | 128/200.21 |
| 4,652,408 | 3/1987 | Montgomery | 128/203.17 |
| 4,767,576 | 8/1988 | Bagwell | 128/200.21 |
| 4,792,097 | 12/1988 | Kremer, Jr. et al. | 128/200.21 |
| 4,819,625 | 4/1989 | Howe | 128/200.14 |
| 4,832,012 | 5/1989 | Raabe et al. | 128/203.17 |

*Primary Examiner*—Clifford D. Crowder
*Assistant Examiner*—Kimberly L. Asher
*Attorney, Agent, or Firm*—Dressler, Goldsmith, Shore, Sutker & Milnamow, Ltd.

[57] ABSTRACT

A nebulizer device with a cooperating disengageable on-line heater device is provided. The nebulizer and the heater together permit one to produce uniformly moisturized gas suitable for inhalation therapy. A relatively large amount of liquid can be entrained in the gas stream that exits the nebulizer device.

15 Claims, 4 Drawing Sheets

NEBULIZER WITH COOPERATING DISENGAGEABLE ON-LINE HEATER

TECHNICAL FIELD

This invention lies in the field of inhalation therapy devices, and, more particularly, in the field of nebulizer devices and heaters therefor.

BACKGROUND OF THE INVENTION AND TECHNICAL PROBLEMS POSED BY THE PRIOR ART

In inhalation therapy, a patient is treated with a gas stream comprised of highly moisturized oxygen, or of highly moisturized admixed air and oxygen. The gas stream is continuously moisturized using a nebulizer device that atomizes either pure water or an aqueous physiological saline solution, with or without added medication. A pressurized oxygen stream is employed in combination with a Venturi device to draw and break up a water stream from a reservoir vessel into an aerosol which is then dispersed throughout the resulting gas stream. The thus moisturized gas stream is delivered through a hose to the patient.

Depending upon such factors as the patient's condition, the objectives of the attending physician, and the like, nebulizer device must provide controlled oxygen content and temperature of the treating gas stream delivered to a patient. Thus, the nebulizing device needs to have the capacity not only to moisturize the treating gas stream, but also to vary, to a desired and controlled extent, the ratio of oxygen to air in the treating gas stream as well as the temperature of the moistened gas stream. Also, it is desirable for the nebulizing device to provide a humidified gas stream generated by it that is substantially free from water droplets larger than those of aerosol size.

The provision of simple, economical, relatively small sized, versatile nebulizer device which can provide all such functions has proven to be very difficult to accomplish in practice. Bulky and complex equipment, heavy power requirements for heating, non-uniform moisturizing and heating, and the like, are commonplace in the nebulizer art.

The art needs simple, reliable, compact efficient, and economical nebulizer apparatus with gas heating capabilities which apparatus can be easily operated, cleaned, and serviced. The present invention satisfies these needs.

SUMMARY OF THE INVENTION

The present invention contemplates an improved nebulizer device that provides a relatively highly moisturized gas output and is provided with a cooperating compact and readily disengageable on-line heater. Heater controls are remote from the heater.

This nebulizer device, suitable for use in inhalation therapy, includes an assembly constituted by a hollow, elongated housing, an elongated manifold body mounted in the housing, an aspirating means as part of the elongated manifold body, a spray deflector means positioned in the path of a spray emanating from the aspirating means, and appropriate gas and liquid connector means for connecting the nebulizer device to a pressurized gas source and a source of the liquid to be nebulized. Preferably a disengageable in-line heater is provided to preheat the liquid stream passing to the aspirating means.

The hollow elongated housing defines a mixing chamber and a serially interconnected droplet disengaging chamber downstream from and disposed at an angle less than a straight angle relative to the mixing chamber. A condensate well is defined at the juncture of these chambers. The mixing chamber is provided with at least one ambient air inlet aperture that is preferably adjustable as to size.

The elongated manifold body extends transversely through the mixing chamber and defines therewithin a nebulizing chamber and communicating gas and liquid channels.

The aspirating means is positioned in the nebulizing chamber and defines therein a pressurizing gas passageway that communicates with the mixing chamber and a liquid passageway that terminates in an annular aperture surrounding the pressurizing gas passageway.

The disengageable heater means is provided with an elongated resistance heating element that is slidably received within a tubular socket situated in the liquid channel that feeds the liquid to be nebulized from the liquid source to the nebulizing chamber.

Such improved nebulizer and heater combination draws a liquid to be nebulized, such as water or an aqueous solution, from an associated reservoir receptacle, and nebulizes the same at a relatively high rate uniformly and controllably with the aid of a pressurized oxygen or air stream. If desired, the resulting aerosol can be further admixed with a controlled volume of air to modulate the oxygen concentration in the humidified gas stream. Also, if desired, the liquid to be nebulized can be controllably heated during its passage from such receptacle to the nebulizer to provide a humidified gas stream having a desired temperature. The nebulizer also is adapted to separate and trap oversized water droplets from the gas stream. Thus, the combination of this nebulizer with this heater provides a uniformly moisturized gas stream wherein the oxygen content, and the temperature, are regulatable with relative ease.

The moisturized gas stream produced by the present nebulizer device provides an aerosol in which the dispersed phase is liquid droplets (e.g. water) and the continuous phase is oxygen or a mixture of oxygen and air. The produced moisturized gas stream initially moves along a flow pathway in the nebulizer which extends initially downwardly, and then upwardly, in an abrupt direction change. Such a flow pathway causes oversized water particles, which are above the colloidal range, to collect and condense on the passageway walls. The resulting condensate runs down along such walls and coalesces in a condensation well located at a gravitationally lowermost portion of the flow pathway. The condensate is returned to the liquid source through a tubular interconnection for reuse. A resulting uniformly moisturized gas stream then exits from the flow pathway within the nebulizer device and passes into a delivery hose or tube for transport to the patient.

In one aspect, the present invention provides an improved nebulizing subassembly wherein a compressed gas stream is passed through an aspirating means which draws water from a water stream derived from an associated reservoir and then breaks up this water stream into droplets that enter into this gas stream. These droplets then strike a spray deflector causing the water droplets themselves to break up into still smaller colloidal-sized droplets that form the desired aerosol. The dynamics of the generated aerosol stream also draw in ambient air to a desired, controlled extent. The operation of this nebulizing assembly is believed to provide a double Coanda effect entraining liquid as well as surrounding gas at about ambient pressure.

In another aspect of the present invention, a new, improved, and simplified construction for a nebulizer is provided which utilizes two principal components, a housing body and a manifold body. Both bodies, and particularly the manifold body, perform various functions. Both bodies are preferably fabricated of plastic and are functionally associated by fabrication procedures such as sonic welding, and the like. A minimum number of separately fabricated starting components are utilized.

In another aspect of the present invention, an improved heating arrangement is provided for achieving a uniformly warmed and moisturized gas stream. Thus, the entering water stream from a supply reservoir is passed in heat exchange relationship, and as a relatively thin film, over outside wall surfaces of a heat exchange tube associated with, and positioned in, the liquid supply pathway. An on-line heater unit having a heat generating cylinder which is electrically and controllably heated is provided and such cylinder is provided with a cooperating housing. The housing and associated heat generating cylinder extend in a coupled and sliding engagement into such heat transfer tube. Exterior surface portions of such heat generating cylinder are thus brought into a proximate and closely spaced relationship to opposing inside wall surfaces of such heat exchange tube. An efficient transfer of thermal energy from such heat generating cylinder to such heat exchange tube is thus achieved, and hence heat is efficiently transfered to the liquid film flowing over the adjacent outside surface portions of such heat exchange tube. The rate of heat transfer to the liquid can be regulated by adjusting the degree of penetration of the heat generating cylinder into the heat exchange tube.

Consequently, a combination assembly of the nebulizer apparatus and of the heater apparatus achieves a uniform, efficient, and controlled heating of water which results in a uniform warming of the resulting moisturized gas stream.

Advantageously, the controls for the operation of the heater device are situated at a remote location from the nebulizer device itself.

When not needed, the heater device can be readily and conveniently slidably detached from the manifold assembly of the nebulizer device.

The heater controls are conveniently arranged. A conventional plug compatible with the available power outlet or receptacle is provided in a control unit for direct insertion into the receptacle to energize the heater device which is connected to the control unit by a cable. The plug is rotatably indexable relative to the power receptacle. A thermistor is employed to provide regulated heating of the liquid stream to be nebulized.

The present invention thus provides a heating unit for use in inhalation therapy which is compact, reliable, accurate, efficient and remotely controllable. The heating unit preheats the water immediately prior to its entering the nebulizer. The heating unit is cooperative with the nebulizer unit and is "plugged in" and functionally positioned in association with the nebulizer unit between the liquid source and the nebulizing components when heating is desired. The heater can be readily detached for nebulizer sterilization and the like. The heater itself need not be sterilized.

Various other and further features, embodiments, and the like which are associated with the present invention will become apparent and better understood to those skilled in the art from the present description considered in conjunction with the accompanying drawings wherein presently preferred embodiments of the invention are illustrated by way of example. It is to be expressly understood, however, that the drawings and the associated accompanying portions of this specification are provided for purposes of illustration and description only, and are not intended as limitations on the invention.

DESCRIPTION OF THE PREFERRED EMBODIMENTS

Referring to FIGS. 1–8, an embodiment of a combination of nebulizer apparatus and heater apparatus of the present invention is designated in its entirety by the numeral 20. The nebulizer apparatus 20 incorporates a housing body 21 which has peripherally enclosing wall means defining an elongated mixing chamber 22 having a first end 23 and a second end 24, and also an elongated droplet disengaging chamber 26 having first end 27 and a second end 28 that terminates in a moisturized gas outlet port. The first end 27 of droplet disengaging chamber 26 is serially integrally interconnected to the second end 24 of the mixing chamber 22. The mixing chamber 22 is angularly disposed relative to the droplet disengaging chamber 26 at an angle less than a straight angle. Preferably the axis 18 of chamber 22 is inclined relative to the axis 19 of chamber 26 at an angle of about 15 to about 45 degrees.

Nebulizer 20 also incorporates an elongated manifold body 29 which extends transversely through the mixing chamber 22 adjacent to the first end 23 thereof.

The manifold body 29, like the housing body 21, preferably is of integral one piece construction, preferably of an injection molded construction. Suitable molding resins include ABS, polycarbonate, high density polypropylene, polyethylene terephthalate, and the like.

The interrelationship between the manifold body 29 and the housing body 21 is such that manifold body 29 is adapted for generally vertical orientation when in use. In such orientation, the associated housing body 21 is positioned so that the mixing chamber 22 extends downwardly from the vicinity of the manifold body 29 to the chamber juncture 30, after which the droplet disengagement chamber 26 extends upwardly to its outlet end 28 to provide a substantially V-shaped configuration. In order to achieve the desired orientation of housing body 21 relative to manifold body 29, the housing body 21 is formed with lower and upper flanged apertures 31 and 32, respectively. The relatively lower aperture 31 is larger in diameter than upper aperture 32 so that, during assembly of nebulizer 20 with the manifold body 29, the manifold body 29 can extend successively through apertures 31 and 32 to achieve the configuration shown in FIG. 2.

Any convenient mounting means can be employed. For example, when the housing body 21 and the manifold body 29 are each comprised of similar or compatible thermoplastic resins, these bodies can be sonically welded together at locations of contact therebetween. For example, circumferentially extending rib 33 is integrally formed with the manifold body 29. Rib 33 has an outside diameter which permits it to slidably pass through a flange 34 that is integrally formed with housing body 21 and outwardly extends circumferentially around the upper aperture 32.

A cover plate 36 is integrally formed circumferentially about the manifold body 29, and plate 36 (FIGS. 2 and 3) is provided with a circumferential perimeter portion that is adapted to mate and engage the terminal edge portions of flange 37 integrally formed with housing body 21. Flange 37 extends downwardly away from and circumferentially around the lower aperture 31. A radially outwardly extending rim 35 which is integrally formed about the perimeter of the cover plate 36 rests against the circumferentially extending edge portions of flange 37 when the housing body 21 and the manifold body 29 are in their assembled configuration (FIG. 2).

The manifold body 29 as formed includes a pair of opposed stems 86 and 87 (FIG. 3) which are axially offset relative to each other, but are axially substantially coplanar. In the mid-region of manifold body 29, stems 86 and 87 join a nebulizing chamber housing 88. The respective functions of stems 86 and 87 and housing 88 are explained below.

To provide structural integrity and strength, the manifold body 29 is provided with a plurality of reinforcing ribs along stems 86 and 87 identified as (proceeding in a top to bottom direction in FIG. 3) ribs 39, 41, 42, 43, 44, and 46. Additional paired supporting ribs 47 for cover plate 36 are also provided. Ribs 47 are positioned at about 90 degrees relative to each of the opposed ribs 42 and 43 about stem 87. Also, paired supporting ribs 48 are provided as added support for reservoir connecting plate 49, the ribs 48 being displaced about 90 degrees from each of the ribs 44 and 46 about stem 87.

Figures 1, 2, 14:
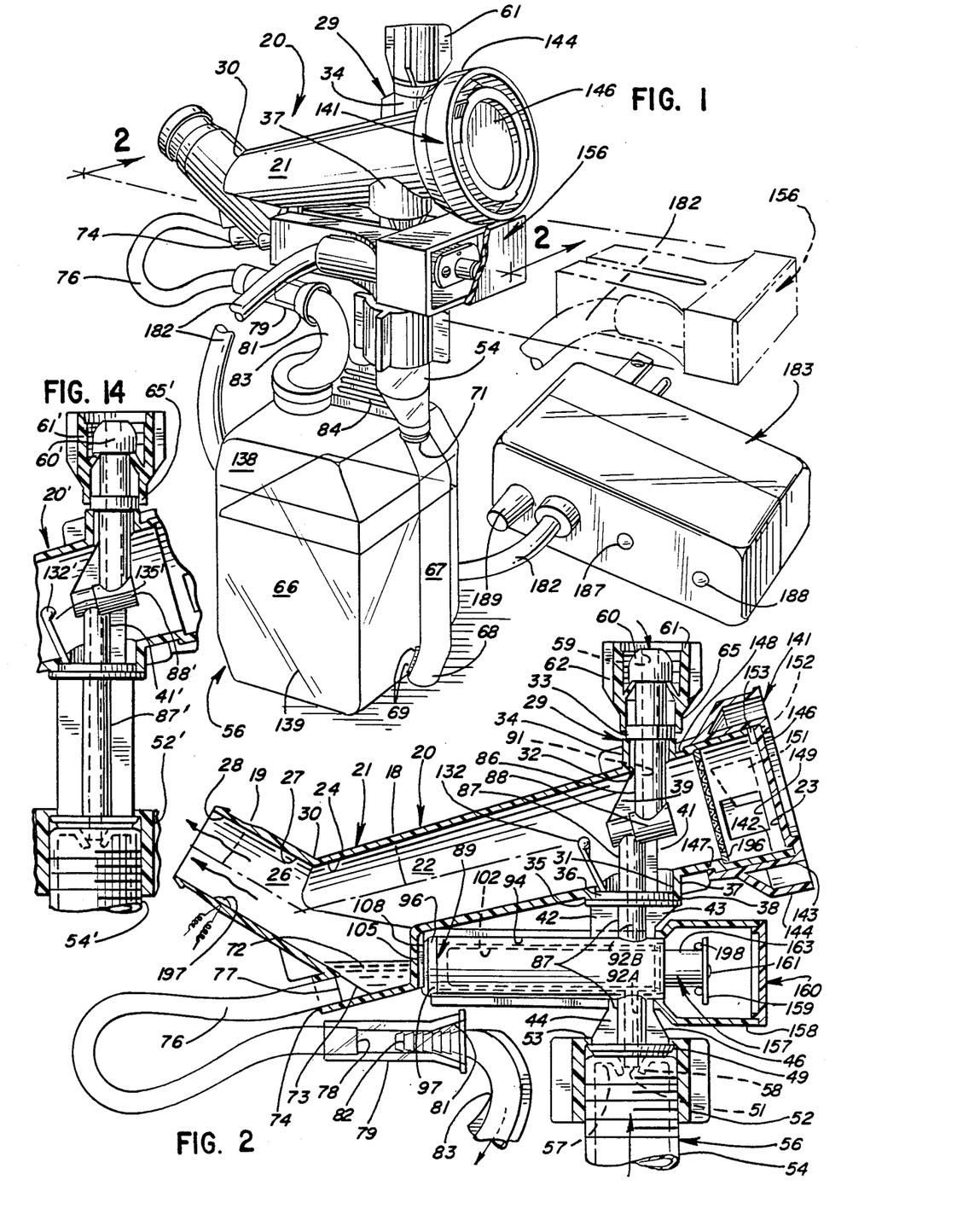
FIG. 1 illustrates an embodiment of one assembled combination of the invention comprising a nebulizer device and associated reservoir container in cooperating association with a disengageable on-line heater device, some parts thereof being broken away to show interior detail, and including a detached phantom illustration showing orientation of such heater device in such combination.
FIG. 2 is a vertical sectional view longitudinally taken generally along the plane 2—2 of FIG. 1 and showing internal aspects of the nebulizer device and of the heater device.
FIG. 14 is a view illustrating an alternative embodiment of a manifold structure of the present invention which cooperates with a housing structure that is similar to that employed in the embodiment shown in FIGS. 1 and 2.
Figures 3, 4, 5, 6:
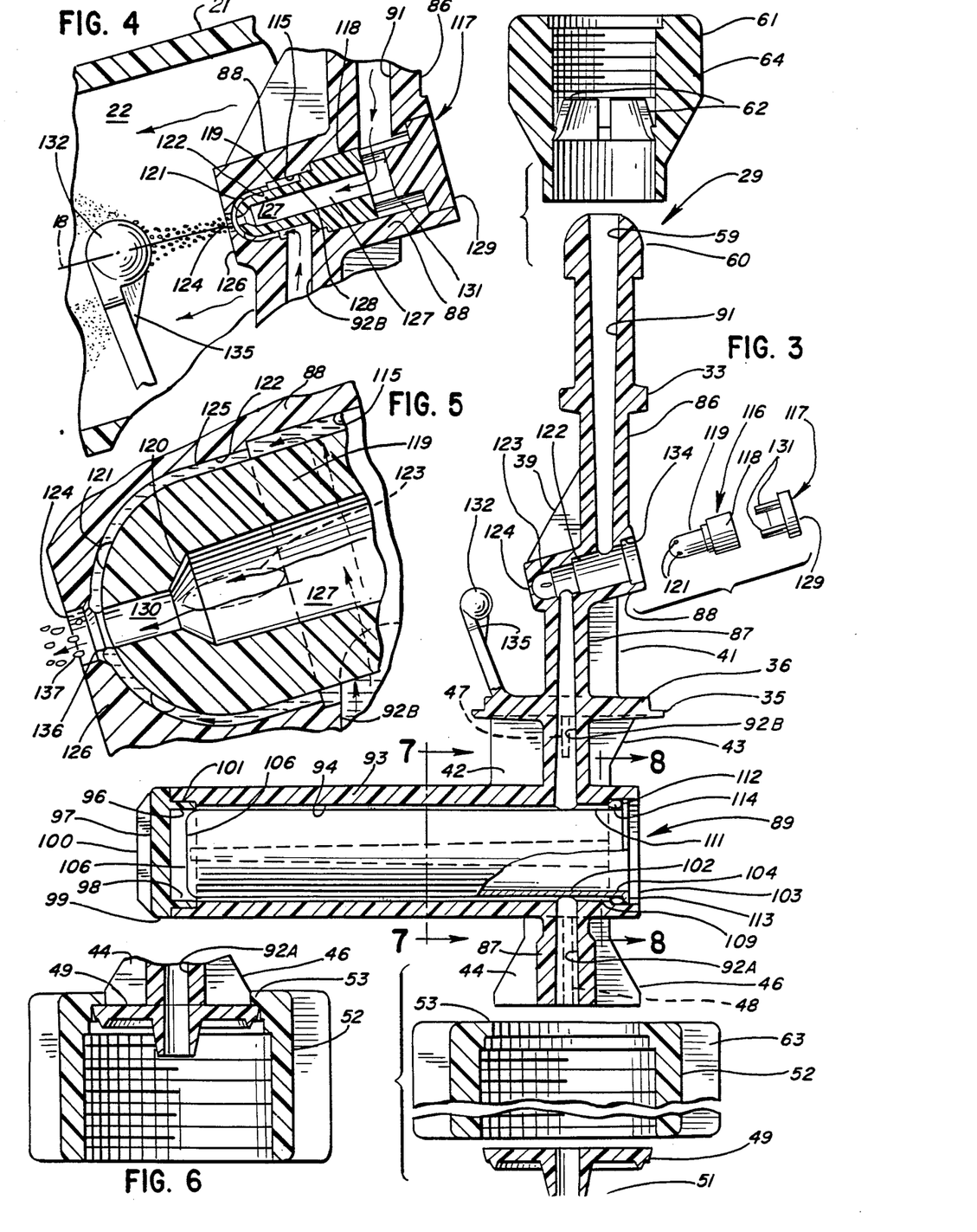
FIG. 3 is an enlarged and exploded vertical sectional view of the manifold structure that is incorporated into the nebulizer device of FIGS. 1 and 2.
FIG. 4 is an enlarged fragmentary vertical sectional view which is partly diagrammatic and which illustrates the structure and operation of a nebulizing zone in the manifold structure.
FIG. 5 is a still further enlarged fragmentary view in vertical section illustrating details of the structure and operation of the aspirating nozzle assembly incorporated into such nebulizing zone.
FIG. 6 is a fragmentary enlarged vertical sectional view of the lower region of the manifold structure shown in FIG. 3.
Figures 7, 8, 12, 13:
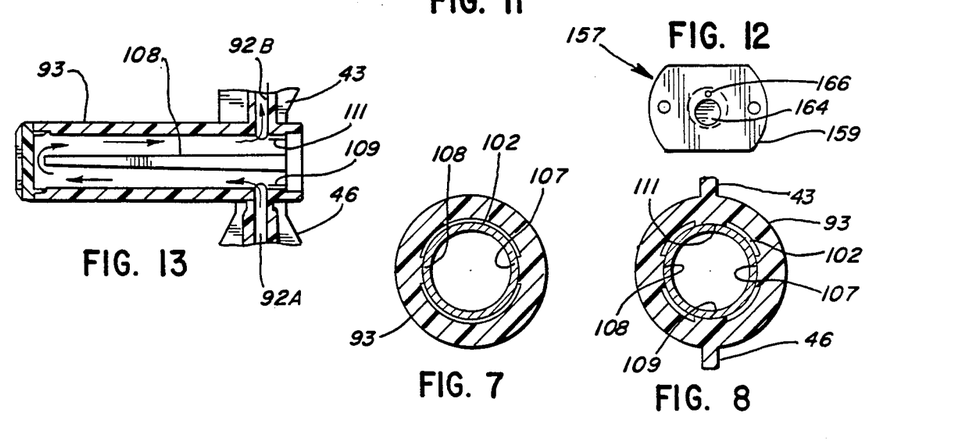
FIG. 7 is a vertical cross sectional view taken generally along the plane 7—7 of FIG. 3.
FIG. 8 is a vertical sectional view taken generally along the plane 8—8 of FIG. 3.
FIG. 12 is a rear end elevational view of the heater core which is incorporated into the heater device of FIGS. 1 and 2.
FIG. 13 is a vertical sectional view with the heater core removed, taken longitudinally through a portion of the manifold structure of FIG. 3 in the region of the liquid heating zone and illustrating the flow pathway of liquid moving through such zone.
Figure 9:
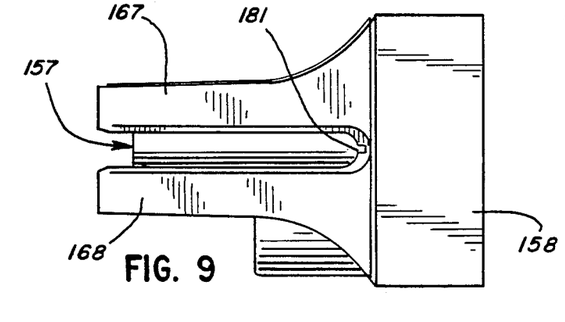
FIG. 9 is a plan view of the housing of the heater device of FIGS. 1 and 2.

The lower end 51 of the stem 87 preferably terminates in a tapering nozzle or spike means that engages a liquid source outlet to facilitate interconnection thereof with a liquid source, such as the receptacle 56 (FIG. 1). For purposes of fabrication and assembly, it is convenient to mold the manifold body 29 with ribs 44, 46 and 48 as well as stem 87 separately formed from the reservoir connecting plate 49 at the lower end 51 of manifold body 29. In assembly, the reservoir connecting plate 49 is first positioned within an internally threaded connecting nut 52 that is provided with an in-turned flange 53 at its rear end (FIG. 6). The flange 53 has an internal diameter sufficient to retain the reservoir connecting plate 49 provided with a secondary wedge-shaped or V-seal within the connecting nut 52.

After such positioning, the connecting plate 49 is placed into an abutting and aligned engagement with the ribs 44, 46, and 48 and stem 87, and then such is sonically welded thereto, or similarly secured. The connecting nut 52 is then freely rotatable about the reservoir connecting plate 49 and is adapted for engagement of manifold body 29 over the mouth 57 at the end of outside threaded neck 54 of reservoir container 56. Outside circumferential edge portions of the reservoir connecting plate 49 have a V-configuration in cross-section and provide a seating engagement with the mouth 57 of the reservoir container or bottle 56, i.e., a secondary seal.

The mouth 57 of bottle 56 can be initially closed by a sealing closure 58, or the like, of the type which is either removable or perforatable and penetratable when a projecting member, such as lower end 51, is forced thereagainst. The connecting nut 52 is threadably connected and tightened about the neck 54 when the nebulizer 25 is engaged with the reservoir bottle 56.

The upper end 59 of the stem 86 of the manifold body 29 is defined by an integrally formed knob 60 of the type insertable into a flexible hose (not shown) to achieve interconnection and sealing engagement between such a connecting hose and the knob 60. To provide a secure clamping engagement between such a hose and knob 60, an internally threaded connecting nut 61 is provided for engagement with the terminus of the hose. Downwardly depending skirt or collar portion 65 enhances the stability of nut 61 when in place. Nut 61 is integrally formed with a plurality of radially inwardly biased conventional flutes 62 about its interior walls which are configured and located so that the nut 61 can be slidably extended over the knob 60 with the edges of the flutes 62 resting against stem 86 and biasing and centering the nut 61 about the base of the knob 60. The nut 61 remains freely rotatable about the knob 60 and available for threadable connection with a conventional coupling (not shown) associated with the connecting hose (not shown).

Each of the nuts 52 and 61 is provided externally with a plurality of circumferentially spaced, longitudinally extending, radially outwardly projecting ribs 63 and 64, respectively, to provide a manual gripping capability for threadably revolving and tightening the respective nuts 52 and 61 during engagement and disengagement thereof.

The reservoir bottle or container 56 is preferably fabricated of a molded semirigid plastic, such as a polyethylene, or the like, and has a generally vertical orientation. Main chamber 66 of bottle 56 defines a reservoir for water an aqueous solution, or the like liquid. Vertically extending along the outside of chamber 66 and unitary with the bottle 56 is a duct 67 which at its lower end 68 communicates with the interior of chamber 66 through a plurality of ducts 69. The upper end 71 of duct 67 is unitary with, and interconnected to, the neck 54.

When the nebulizer 20 is associated with bottle 56 so that the nut 52 threadably interconnects the manifold body 29 with the bottle neck 54, the manifold body 29 is generally in the upright or vertical configuration shown in FIGS. 1 and 2. In this configuration, and as indicated above, the elongated mixing chamber 22 descends proceeding from the region of the manifold body 29 therein toward juncture 30, and the droplet disengaging chamber 26 ascends proceeding from juncture 30 in housing body 21. In this manner, an angle less than a straight angle is formed between channels 22 and 26. In this configuration, a condensation well 72 is defined in the resulting gravitationally lowermost region between the chambers 22 and 26 and below the flow path of the moisturized gas stream exiting the nebulizer device. During operation of the nebulizer 20, a liquid condensate which reaches condensation well 72 can exit therefrom through a flanged orifice 73 and is returned to the liquid supply in bottle 56.

Communicating with the mouth of a flange 74 that is integrally formed with orifice 73 is the end 77 of a flexible tube 76.

The opposite end 78 of tube 76 is associated with a connector 79 which is provided with a funnel configured mouth 81. Connector 79 is adapted for rapid connection and disconnection with the notched distal end 82 of goose neck 83. The goose neck 83 is integrally formed with, and functionally joined to, the reservoir bottle 56. Thus, condensate from well 72 can flow trough tube 76, connector 79, and neck 83 back into chamber 66. Duct 67 is unitary with chamber 66. A septum 84 extends between lower adjacent portions of goose neck 83 and neck 54 providing support and rigidification therefor.

In the manifold body 29, each of the stems 86 and 87 define a channel 91 and 92, respectively, extending therethrough longitudinally so that the lower end 51 interconnects with the chamber housing 88 by channel 92. The upper end 59 connects with the nebulizing chamber housing 88 by channel 91.

The channel 92 is interrupted in its mid-region by an altered flow pathway. Such altered flow pathway and interruption occur in the region of a heat exchanger assembly which is of the shell and tube type and is designated in its entirety by the numeral 89. In the heat exchanger 89, liquid from the lower portion of channel 92, which portion is herein designated for convenience by the numeral 92A, flows into the shell portion of heat exchanger 89, and then re-enters the upper portion of the channel 92, which portion is herein designated for convenience by the numeral 92B.

As can be seen, for example, in FIGS. 3 and 6, heat exchanger 89 incorporates cylindrical shell wall portions 93 which are integrally formed with the stem 87 when the manifold body 29 is molded. When the distal end 96 of the cylindrical wall portions 93 is closed by a cap plate 97, a cylindrical cavity 94 is defined. In the embodiment shown, the cap plate 97 is provided with an integrally formed, circumferentially extending, axially projecting flange 98 (FIG. 3) which is radially inset from the periphery 99 of plate 97 so that the flange 98 can be received within the corresponding internal circumferential recess 101 about distal end 96. When the cap plate 97 is slidably engaged with the circumferential wall 93 in the manner shown, for example, in FIG. 3, the flange 98 can be sonically welded or otherwise attached to the shell wall portions 93 in the region of the recess 101 to provide an integrally formed structure.

Figure 11:
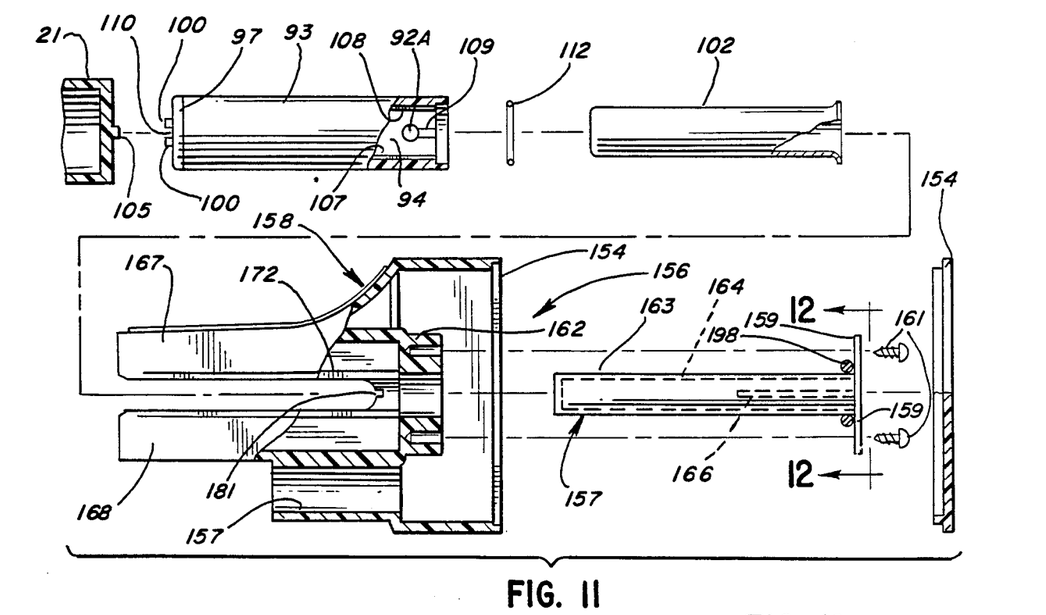
FIG. 11 is an exploded plan view of the elements comprising the heater device of FIGS. 1 and 2 which are shown in combination with a cooperating portion of the manifold structure of FIG. 3.
Figures 15, 16:
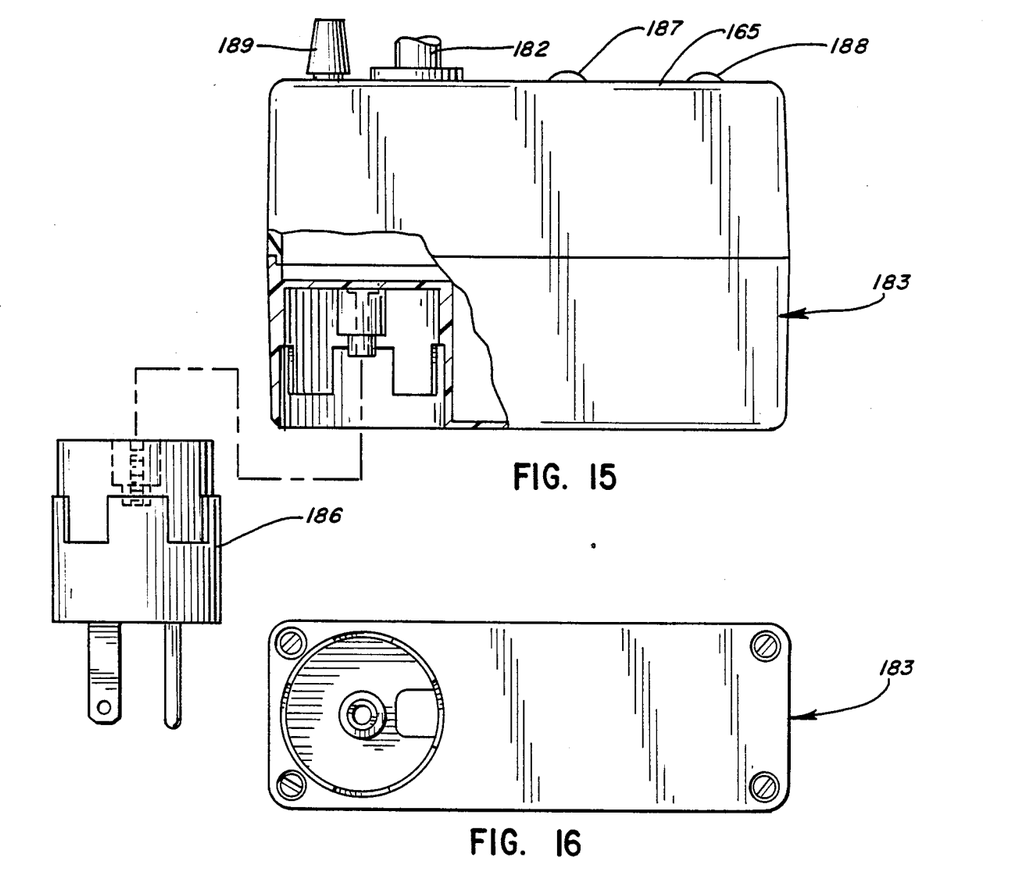
FIG. 15 is a plan view of the receptacle plug and control unit assembly which is used in cooperation with the heater device of this invention, some parts thereof being broken away, and some parts thereof being shown in section.
FIG. 16 is an end elevational view of the back wall of the assembly shown in FIG. 15 with the electrical outlet connecting indexing turret assembly removed.

To rigidify and strengthen manifold body 29 and integrally associated heat exchanger 89, the outside face of cap plate 97 (FIGS. 2 and 3) is formed to include a pair of spaced, parallel diametrically extending ribs 100 which, when cap plate 97 is installed over distal end 96, are oriented parallelly to channel 92 and stem 87. The groove 110 (FIG. 11) defined between the ribs 100 is adapted to make mating engagement with a rib 105 (FIGS. 2 and 11) integrally formed on housing body 21 when the housing body 21 and the manifold body 29 are assembled. The rib 105 is positioned adjacent the region of second end 24 of chamber 22 where the wall portion of housing body 21 is angled and extended to provide a base surface on which to position the rib 105 for aligning the rib 105 with the ribs 100. Such an angling of housing body 21 in such region also serves to further define the condensation well 72 and assists in collection of undesirable oversize droplets.

Within the cavity 94 thus defined by cylindrical wall portions 93 and cap plate 97, a metallic tubular member 102 is inserted through the open proximal end 103 of cylindrical wall portions 93, as shown in FIG. 3. The tubular member 102 has an open end 104 for receiving a heat generating cylinder 157 and a closed end 106. The tube 102 can be formed of a metal, such as stainless steel, or the like. Interior surface portions of the cylindrical wall 93 are provided with radially inwardly projecting ribs 107 and 108 (see FIG. 11, for example) which longitudinally extend in opposed relationship relative to one another at approximately a 90 degree spacing relative to channel 92 (both upper portion 92B and lower portion 92A). Additionally, ribs 109 and 111 on interior surface of wall 93 extend from each of the respective channels 92A and 92B to the proximal end 103.

When the tube 102 is positioned in the cavity 94, a sealing means, such as an O-ring seal 112, is circumferentially located around the outside of the open end 104 of tube 102 adjacent an out-turned flange 113 formed on tube 102. The O-ring seal 112 is adapted to make a seating and sealing engagement circumferentially around a recessed area 114 defined at the proximal end 103 of cavity 104 in the cylindrical wall portions 93. Thus, when the tubular member 102 is in position within the cavity 94, the tubular member 102 is supported in spaced relationship to interior wall portions of the cylindrical walls 93 by the ribs 107, 108, 109 and 111. Also, the combination of the O-ring seal, which is in sealing engagement with the cylindrical wall portions 93, with such ribs 107, 108, 109 and 111 defines a flow pathway whereby a thin film of liquid from the lower channel 92A entering the heat exchanger 89 is formed and is moved through the heat exchanger 89 in adjacent relationship to outside wall surface portions of the metallic tube 102. After such a circulation, the liquid in the shell portion of the heat exchanger 89 exits from the heat exchanger 89 and enters the channel 92B. Liquid in channel 92B can continue to move upwardly into the interior of the nebulizing chamber housing 88.

A compressed gas such as oxygen or air entering the channel 91 through upper end 59 moves through the channel 91 into the nebulizing chamber housing 88.

The nebulizing chamber housing 88 is internally configured to receive therewithin a liquid delivery element 116 and a gas delivery element 117 (see FIG. 3) which are generally coaxially aligned and in serial relationship with respect to one another. The liquid delivery element 116 is provided with a socket portion 118 and with a forward and integral annulus forming stem member 119. The region around the tip of stem 119 is provided with a plurality of circumferentially spaced blossom points or spacers 121. The liquid delivery element 116 is adapted to be matingly received within a forward portion of the cavity 122 defined by housing 88. Preferably cavity 122 has a substantially hemispherical configuration to provide a uniform delivery of liquid film 125 around an orifice at the outermost or distal end of channel 130 as best seen in FIG. 5. The hemispherical configuration enhances aerosol particle size uniformity and output rate. Conveniently, forward wall portions of the cavity 122 are provided with a plurality of short longitudinally extending, radially inwardly projecting ribs 123 (FIG. 5).

When the liquid delivery element 116 is inserted into the cavity 122, the assembled configuration shown generally in FIGS. 4 and 5 is assumed between the liquid delivery element 116 and the nebulizing chamber housing 88. When a liquid such as water is delivered into cavity 122 at the terminus of a liquid passageway from channel 92B (see FIG. 5, for example), the liquid fills the annular space between housing 88 and stem 119.

Upstream from cavity 122 is provided an annular well 115 which permits the maintenance of an uninterrupted supply of liquid to cavity 122 during nebulizer use. Well 115 preferably has a volume of at least about three times that of cavity 122. Annular well 115 is defined by nebulizing chamber housing 88 and an intermediate portion of liquid delivery element 116. The spacing between element 116 and housing 88 can be fixed or adjustable, as desired.

A single aerosol discharge orifice 124 is defined in a forward wall 126 of housing 88. The orifice 124 preferably has a diameter in the range of from about 0.02 inch to about 0.08 inch. Owing to the relationship between the stem 119 and adjacent wall portions of the housing 88, an annular region or layer of water 136 is provided circumferentially about the side edge portions of the forward wall 126 adjacent the orifice 124. The ribs 123 and the spacers 121 coact to position, center, and orient the liquid delivery element 116 to define the annular and substantially hemispherical cavity 122 between the housing 88 and the stem 119. Liquid can thus flow continuously from channel 92B to form a liquid film 125 surrounding the orifice 124 with a gas-liquid boundary 136.

Axially extending through the stem 119 of liquid delivery element 116 is a channel 127 which is provided with slightly forwardly tapering side walls 128 except adjacent the forward tip region of stem 119 where the channel is reduced by tapering over a relatively short length 120 to provide a gas channel 130 that is about one-half the size of the aerosol discharge orifice, i.e., about 0.04 inch to about 0.01 inch in diameter. The gas exit orifice define by channel 130 is in substantial registry with aerosol discharge orifice 124.

The gas delivery element 117 is provided with a base plate 129 from which upstands a plurality of circumferentially spaced, forwardly and longitudinally extending legs 131. The base 129 is adapted to be circumferentially received within a rear aperture 134 having an enlarged mouth portion in the housing 88 with the forward ends of the respective legs 131 being in abutting engagement with the bottom of the socket 118 of water delivery element 116. When liquid delivery element 116 and gas delivery element 117 are in their assembled configuration and mounted within the housing 88, the base 129 and associated contacting regions are conveniently sonically welded to the housing 88 at adjacent portions therebetween to provide an integrally formed structure.

Compressed gas flowing in channel 91 thus passes between the legs 131 and enters the channel 127 which extends through the socket 118. Hence, gas can flow continuously from channel 91 through channel 130 in stem 119, and out through aerosol discharge orifice 124 downstream from channel 130.

A spray deflector means, here shown as a spherical member 132, preferably with a wedge-like portion 135 underneath, is located so as to be in general axial alignment with the flow axis of a gas stream issuing from the orifice 124. Although a spherical configuration is illustrated, other geometrical shapes for such deflector means, such as a pyramid-like configuration, or the like, can be utilized. The spherical body 132 is supported by a diagonally extending leg 133 which projects upwardly and outwardly from cover plate 36. The spherical member 132 and the leg 133 are conveniently and preferably integrally formed during the molding of the manifold body. However, if desired, the leg 133 and the member 132 can be separately formed and mounted as shown, for example, in FIGS. 2 and 3 using a sonic welding procedure, or the like.

When the nebulizer device 20 is operably communicating with a reservoir bottle 56 and with a source of compressed gas, e.g. oxygen, pressurized gas is fed from end 59 through channel 91 into the housing 88. The interrelationship between the components is such that the pressurized gas stream passing the gas-liquid boundary 136 entrains the contiguous liquid and causes additional liquid to be drawn upwardly or aspirated from bottle 56 through the channels 92A and 92B and through shell side of the heat exchanger 89. Pressure in the head space 138 existing in bottle 56 over the level of the liquid 139 contained in bottle 56 is maintained at about atmospheric as the liquid is withdrawn through duct 67 on its pathway towards orifice 124 by venting into space 138 through tube 76. Such a venting arrangement also assists in return of the liquid from well 72 to the bottle 56. The pressurized gas stream flowing through the orifice 124 generates droplets of water from the region of boundary 136 and disperses and entrains the generated droplets in the pressurized gas stream issuing from the orifice 124.

These water droplets 137 which are thus drawn and separated from the liquid film 125 travel forwardly in the gas stream and impinge upon member 132 as well as wedge-like portion 135 both of which are in the gas stream flow path. The relationship between the size of the member 132 and the distance of the member 132 from the orifice 124 are such that a major portion (preferably at least about 75% by volume) of the liquid droplets 137 emerging from the orifice 124 strike the member 132. In so doing, the droplets 137 break up into aerosol-forming droplet sizes which disperse into the adjacent gas stream and thereby form an aerosol.

Atmospheric air is admitted into the mixing chamber 22 at end 23. The pressure differential in the region of the spray deflector 132 is such that a slightly subatmospheric pressure exists thereabouts in normal operation of the nebulizer 25 so that air is drawn into this region from the mixing chamber end 23.

In order to regulate the ratio of oxygen to air (when oxygen is the gas used in forming an aqueous aerosol), the nebulizer 20 is provided with a rotatable cover member or slip closure 141 which extends over first end 23 and down along outside wall portions 142 of body 21 adjacent first end 23.

For purposes of mounting the cover member 141 over and around first end 23, the wall portions 142 adjacent thereto are slightly radially enlarged (see, for example, FIG. 2) relative to subsequent wall portions. The cover member 141 is provided with an inside or interior circumferentially extending wall portion 143. A radially spaced but coaxial outer circumferentially extending wall portion 144 is provided as well. The relationship between wall portions 143 and 144 is such that the outer circumferential wall portion 144 tapers and connects integrally with the interior circumferential wall portions 143 in longitudinally spaced relationship to the first end 23. A cap plate 146 with a sunken center and a circumferential groove adjacent to wall portion 143 is integrally formed across the interior circumferential wall portions 143. Plate 146 functions to seal the end 23. The interior surfaces of wall portions 143 are adapted to be slidably mounted over outside wall portions of the enlarged area 142 with the cap plate 146 fully received over end 23.

After being so positioned, a circumferentially extending, radially inwardly projecting lip 147, terminally located in wall portion 144 and integrally formed therewith, snaps into a circumferentially extending recess 148 extending around the back end of enlarged wall portions 142, which serves to retain the cover member 141 in position about wall portions 142 of housing body 21 and adapted for rotational movements. To limit rotational movements of cover member 141, a circumferential slot or groove 153 is formed in end 23 within which is received a stop plug 152 formed in the circumferential groove of cap plate 146.

The circumferential outside wall portions 144 are provided with circumferentially spaced, longitudinally extending, integrally formed rib portions (not shown) to facilitate manual rotation of the cover member 141.

A plurality (here two) of generally rectangularly configured slots 149 are formed in the enlarged area 142 in circumferentially uniformly spaced relationship to one another. A plurality of corresponding, alignable, and generally trapezoidally configured apertures 151 are provided in the interior circumferential wall portions 143. Such trapezoidal apertures 151 are in circumferentially equally spaced relationship to one another. Thus, when the cover member 141 is revolved about the enlarged area 142, variations in the sizes of the resulting composite apertures formed by the overlayment of individual apertures 151 over corresponding slots 149 are achieved so that the volume of air admitted into the first chamber 22 is determined and made controllably variable by the total cross-sectional aperture area open to atmospheric air at any given time (as specifically determined by the angular relationship between the cover member 141 and the enlarged area 142 of body 21).

The cover member 141 is calibratable, so that an operator can merely adjust the relative position of the cover member 141 in relation to the housing 21 according to a calibrated index (that can, for example, be marked on body 21 adjacent to wall portions 143) to achieve a desired ratio of air to oxygen in a moisturized gas stream generated in the first chamber 22 for a given pressurizing gas pressure. When the cover member 141 is in its closed configuration, there is no overlap between the slots 149 and the trapezoidal apertures 151, so that the moisturized gas mixture formed in chamber 22 is constituted substantially by oxygen and water droplets. At the other extreme, when the slots and trapezoidal apertures are in full registration with one another, a maximum amount of air is admitted into the mixing chamber 22, and relatively little oxygen concentration enhancement is provided in the thus-produced moisturized gas stream.

As indicated above, the moisturized gas stream produced in the chamber 22 comprises an aerosol wherein the dispersed phase is liquid droplets, e.g. water, and the continuous phase thereof is oxygen or a mixture of oxygen and air. After its formation, such moisturized gas stream initially moves along a flow pathway which extends downwardly in mixing chamber 22 and then, after juncture 30 is passed, extends upwardly. Such a flow pathway is effective in causing oversized water particles, that is particles which are above the colloidal range in size, to coalesce primarily on the interior walls of mixing chamber 22 and also on the walls of droplet disengagement chamber 26. In particular, the angle formed at juncture 30 traps oversize droplets and directs them to well 72. The gas mixture issuing from the end 28 of chamber 26 is substantially uniformly moisturized or humidified and suitable for patient utilization. Liquid collected in well 72 is returned into the reservoir bottle 56, as above explained.

An optional entrainment filter 196 can be provided downstream from air inlet apertures or slots 149 but upstream from manifold 29. This filter can be a 250-micron filter effective to retain dust and lint and at the same time contain liquid droplets within mixing chamber 22.

When it is desired to provide a heated moisturized gas stream emerging at end 28 of nebulizer apparatus 25, the water circulated through the shell side the heat exchanger 89 (as above explained) is heated. The heating is accomplished by first slidably engaging a heater assembly 156 with the heat exchanger 89. The heater assembly 156 (see, for example, FIGS. 9-12) utilizes a heater member 157 provided with a cylindrical core portion 163 which serves as a heat generating cylinder and is adapted to be slidably received into tube 102, thereby placing interior wall surface portions of the tube 102 into a close approximate adjacent relationship with exterior wall portions of the cylindrical core portion 163 provided with O-ring seal 198 at the plate 159. When the core portion 163 is electrically heated, heat is transferred efficiently into and through the metallic tube 102, thereby heating the water flowing over outside wall surfaces of the tube 102 in the heat exchanger 89. Heat transfer rate can be adjusted by adjusting the length of core portion 163 that is received within tube 102.

The heater member 157 is centrally mounted in housing 158 which is preferably formed of an integral one piece molded body. Suitable heat resistant plastics for use in fabricating the housing 158 include filled polycarbonates, polyamides, polyimides, polyesters, phenolic resins, and the like.

Figure 17:
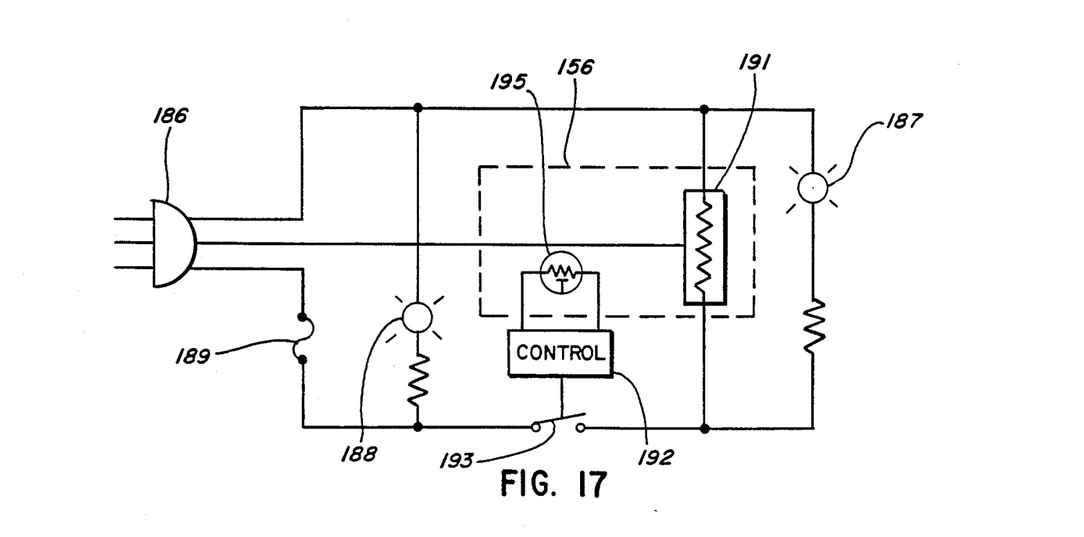
FIG. 17 is an illustrative wiring diagram of the heater apparatus utilized in the embodiment shown in FIGS. 1 and 2.

The heater member 157 is provided with an integrally formed transversely extending base plate 159 located at one end thereof (FIGS. 11 and 12) which plate 159 is adapted for mounting by means of paired screws 161 to a support plate 162 in housing 158. As thus mounted, the cylindrical core portion 163 is otherwise unsupported and thereby is adapted to extend into tube 102 through open end 104 thereof. For reasons of facilitating the controlled heating of the core portion 163, an eccentric bore 164 is provided in the core portion 163. Adjacent to the bore 164 in the solid thickened portion remaining in core portion 163 another and smaller bore 166 is provided for mounting a thermistor 195 (FIG. 17). Thus, in assembled heater assembly 156, a calrod or like electrically heated rod is positioned within the eccentric bore 164 and the thermistor 195 is positioned into the adjacent relatively smaller bore 166 to sense temperatures generated in the core portion 163 of heater member 157. The amount of power fed to the heat generating element is controlled by conventional control circuitry 192 that receives input from thermistor 195.

An optional thermistor 197 (FIG. 2) providing feedback to control 192 can be provided in droplet disengagement chamber 26, if desired.

Preferably core portion 163 is formed of a metal, such as brass or the like, and provides a heat sink for the resistance heating element contained therewithin.

The housing 158 not only provides a safety device for maintaining a protective barrier between an operator and the hot portions of the heater assembly 156 and of the nebulizer 20, but also makes possible easy engagement and disengagement of the heater assembly 156 with the heat exchanger 89 without electrical interconnection to the nebulizer itself.

Figure 10:
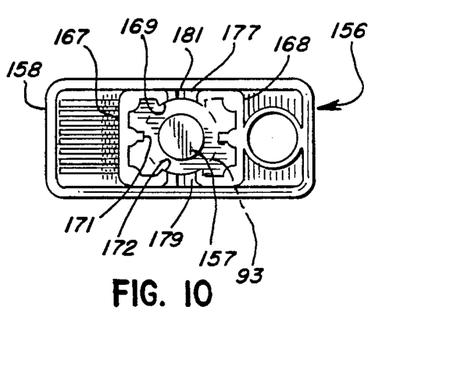
FIG. 10 is a forward end elevational view of the assembled heater device of FIGS. 1 and 2 with the position of the heat exchanger housing in the assembled combination of nebulizer and heater shown in phantom.

Thus, housing 158 is provided with two forwardly extending beams 167 and 168 which are supported on opposing sides of core portion 163 by the rear portions of housing 158. As shown in FIG. 10, each beam 167 and 168 is provided with three depending elongated ribs designated as ribs 169, 171, and 172 in beam 167 and as ribs 173, 174, and 176 in beam 168. These beams and their respective associated such ribs are thus configured so as to extend over, and slidably move over, outside wall surfaces of the cylindrical shell wall portions 93 of heat exchanger 89 with the respective such ribs being used for spacing, centering, and guidance.

Concurrently, slots 177 and 179 which longitudinally extend between the respective beams 167 and 168 are configured so as to permit transverse extension of the stem 87 therethrough. When the housing 160 has been fully slidably engaged about the heat exchanger 89, terminal grooves 181 (paired, one in the base of each slot 177 and 179) as shown, for example, in FIGS. 9 and 11) defined in housing 160 receive and engage ribs 43 and 46 of the manifold body 29. In the fully interengaged relationship between the heater assembly 156 and the shell and tube-type heat exchanger 89, a stabilized and mutually interlocking type of relationship is achieved.

The heater assembly 156 is connected to a control unit 183 by means of a cable 182.

Control unit 183 is equipped with a plug 186 which is adapted to be indexed at 90 1069 degree intervals through four positions with each position being suitable for operating the control box with a differing receptacle position. Indexing is accomplished by means of loosening a screw (not shown) inside box 183, and then manually extending turning, i.e., indexing, the plug 186 to a new desired position which will permit the control box 183 to accept the line voltage available at the use site.

The control unit 183 is equipped with a pilot light 188 which is in a normally on position when the plug 186 is inserted into an electrical outlet (not shown) capable of supplying power. The control box 183 also is provided with a warning light 187 which is in a lighted condition when the heating element 191 is energized.

A simplified wiring diagram for the electrical heater apparatus of this invention is illustrated in FIG. 17. When plug 186 is energized, the line switch is closed, and the calrod heating element 191 is activated. The thermistor 195 activates control 192 which serves to regulate power supplied to the resistance heating element 191 in the core member 157 and thereby maintain the temperature of core member 157 at a chosen set point. Usually the set point is selected so as to provide the patient with moisturized gas at about body temperature, i.e., about 98° F.; however, the set point can be selected as required for a particular intended application. When the set point is reached as determined by thermistor 195, the circuit is opened by the opening of line switch 193 by the thermistor-activated control unit 192, and no more electrical energy is supplied to the heating element 191 until sufficient cooling occurs as sensed by thermistor 195 to require additional electric energy to maintain the set point temperature in the core portion 163 of heater member 157, at which time, the control unit 192 again closes the line switch 193.

The manifold body 29 in the combination thereof with housing body 21 can be replaced if desired by a manifold body, such as manifold body 194 shown in FIG. 14, if a heater is not desired. Such a manifold body 194 may be used, for example, when no warming of a moisturized gas stream is contemplated, or when some other means or procedure is contemplated for use with a nebulizer of this invention to achieve a warmed, moisturized gas stream. The manifold body 194, except for the absence of the heater assembly 156, is similar to the manifold body 29 in structure and function. Portions of manifold body 194 which correspond to portions of manifold body 29 are similarly numbered, but with the addition of prime marks thereto.

Although the present invention has been described and illustrated based on the presently available information and embodiments, it is to be understood that modifications and variations are within the spirit and scope of the invention, as those skilled in the art will readily appreciate, and that such are within the purview and scope of the appended claims.

We claim:

1. A nebulizer device for use in inhalation therapy comprising in combination:
   (a) a hollow, elongated housing defining a mixing chamber communicating and serially interconnected with a droplet disengaging chamber, disposed relative to said mixing chamber at an angle less than a straight angle; said mixing chamber having an ambient air inlet aperture and said droplet disengaging chamber having an outlet port;
   (b) an elongated manifold body mounted in said housing and extending transversely through said mixing chamber; said manifold body defining therewithin:
      (1) a nebulizing chamber situated in a mid-region thereof,
      (2) a gas conducting channel extending from one end of said manifold body to said nebulizing chamber and communicating therewith,
      (3) a liquid conducting channel extending from the opposite end region of said manifold body to said nebulizing chamber and communicating therewith; and
      (4) aspirating means positioned in said nebulizing chamber and defining in combination with said nebulizing chamber:
         (i) a gas passageway for conducting a pressurized gas stream from said gas conducting channel to a gas orifice which opens into said mixing chamber in a direction generally towards said disengaging chamber;
         (ii) a liquid passageway for conducting a liquid stream from said liquid conducting channel to an annular opening located in said nebulizing chamber adjacent to said gas orifice and extending circumferentially thereabout; and
         (iii) a aerosol discharge orifice in substantial registry with said gas orifice and downstream therefrom; the interrelationship between said gas orifice and said annular opening being such that a pressurized gas stream issuing from said gas orifice entrains droplets of said liquid stream from said annular opening and disperses entrained droplets in said so issuing pressurized gas stream;
   (c) a spray deflector means located in said mixing chamber and in the path of said so issuing gas stream from said aerosol discharge orifice, the relationship between the size of said spray deflector and the distance thereof from said aerosol discharge orifice being such that a major portion of liquid droplets emerging from said aerosol discharge orifice in such gas stream strike said spray deflector means, thereby breaking up said spray droplets into an aerosol which disperses into the issuing gas stream;
   (d) gas connector means for connection of said gas conducting channel to a source of pressurized gas;
   (e) liquid connector means for connection of said liquid conducting channel to a source of liquid to be nebulized and situated below said nebulizer device; and
   (f) a transversely extending heat exchanger means in said liquid conducting channel, said heat exchanger means comprising:
      (i) a hollow tubular member having an open end and a closed end;
      (ii) a chamber circumscribing wall portions of said tubular member, said circumscribing chamber being integral with said manifold body and having interior wall surfaces which are provided with inwardly projecting rib portions adapted to define a flow path for liquid moving through said liquid conducting channel and to provide wall spacing means for centering said tubular member therewithin; and
      (iii) sealing means circumferentially located around the outside of said tubular member for providing a sealing engagement between said tubular member and said chamber wall portions circumferentially adjacent said open end, whereby such combination coacts to circulate a liquid received from said liquid channel as a relatively thin layer over exterior wall surface portions of said tubular member.

2. The nebulizer device of claim 1 wherein a heater means is slidably received within said heat exchanger means.

3. The nebulizer device of claim 2 wherein heater means comprises:
   (a) a core member adapted to be slidably received into said hollow tubular member through said open end thereof;
   (b) resistance heating means in said core member;
   (c) temperature sensing thermistor means in said core member; and
   (d) housing means for said core member.

4. The nebulizer device of claim 1 wherein said heater means further includes a remote control unit.

5. A nebulizer device for use in inhalation therapy comprising in combination:
   (a) a hollow, elongated housing defining a mixing chamber communicating and serially interconnected with a droplet disengaging chamber, disposed relative to said mixing chamber at an angle less than a straight angle; said mixing chamber having an ambient air inlet aperture and said droplet disengaging chamber having an outlet port;
   (b) an elongated manifold body mounted in said housing and extending transversely through said mixing chamber; said manifold body defining therewithin;
      (1) a nebulizing chamber situated in a mid-region thereof,
      (2) a gas conducting channel extending from one end of said manifold body to said nebulizing chamber and communicating therewith,
      (3) a liquid conducting channel extending from the opposite end region of said manifold body to said nebulizing chamber and communicating therewith; and
      (4) aspirating means positioned in said nebulizing chamber and defining in combination with said nebulizing chamber:
         (i) a gas passageway for conducting a pressurized gas stream from said gas conducting channel to a gas orifice which opens into said mixing chamber in a direction generally towards said disengaging chamber;

(ii) a liquid passageway for conducting a liquid stream from said liquid conducting channel to an annular opening located in said nebulizing chamber adjacent to said gas orifice and extending circumferentially thereabout; and (iii) an aerosol discharge orifice in substantial registry with said gas orifice and downstream therefrom; the interrelationship between said gas orifice and said annular opening being such that a pressurized gas stream issuing from said gas orifice entrains droplets of said liquid stream from said annular opening and disperses entrained droplets in said so issuing pressurized gas stream; said aspirating means being comprised of a water delivery element and a gas delivery element which coact with said nebulizing chamber and which are serially and coaxially positioned relative to one another in said nebulizing chamber with said water delivery element being in adjacent relationship to said gas orifice, and with a top region of said gas delivery element abutting against bottom portions of said water delivery element; said water delivery element in combination with said nebulizing chamber defining said liquid passageway adapted to provide substantially uniform liquid delivery to said annular opening; and said gas delivery element in combination with said nebulizing chamber and said water delivery element defining said gas passageway adapted to provide gas delivery to said gas orifice;

(c) a spray deflector means located in said mixing chamber and in the path of said so issuing gas stream from said aerosol discharge orifice, the relationship between the size of said spray deflector and the distance thereof from said aerosol discharge orifice being such that a major portion of liquid droplets emerging from said aerosol discharge orifice in such gas stream strike said spray deflector means, thereby breaking up said spray droplets into an aerosol which disperses into the issuing gas stream;

(d) gas connector means for connection of said gas conducting channel to a source of pressurized gas; and (e) liquid connector means for connection of said liquid conducting channel to a source of liquid to be nebulized and situated below said nebulizer device.

6. The nebulizer device of claim 5 wherein said elongated manifold body is adapted to be generally vertically oriented when said liquid connector means is so connected to such a liquid source, and, when said manifold body is so oriented, then said mixing chamber slopes away from said manifold body downwardly to said droplet disengaging chamber and said droplet disengaging chamber slopes upwardly from the juncture thereof with said mixing chamber, thereby permitting liquid droplets to collect in the gravitationally lowest region which defines a condensation well at the juncture of said mixing and said droplet disengaging chambers, said nebulizer device further including conduit means interconnecting said condensation well with said reservoir means whereby condensate collected in said region drains into said liquid source.

7. The nebulizer device of claim 5 wherein said spray deflector means is generally spherically configured.

8. The nebulizer device of claim 5 wherein the liquid passageway provided substantially uniform liquid delivery to said annular opening has a substantially hemispherical configuration.

9. The nebulizer device of claim 5 wherein said liquid passageway is downstream from an annular liquid well and is in liquid communication therewith.

10. The nebulizer device in accordance with claim 5 wherein said liquid passageway terminates in a substantially hemispherical cavity that surrounds said gas orifice.

11. The nebulizer device in accordance with claim 10 wherein said substantially hemispherical cavity is in direct communication with an annular well having a volume capacity at least three times that of the hemispherical cavity.

12. The nebulizer device in accordance with claim 5 wherein said elongated manifold body includes in said liquid conducting channel, and in communication therewith, a transversely extending heat exchanger for heating the liquid passing through said liquid conducting channel.

13. The nebulizer device in accordance with claim 12 wherein a heater means is slidably received within said transversely extending heat exchanger.

14. The nebulizer device in accordance with claim 12 wherein said heater means further includes a remote control unit.

15. A nebulizer device for use in inhalation therapy comprising in combination:

(a) a hollow, elongated housing defining a mixing chamber communicating and serially interconnected with a droplet disengaging chamber, disposed relative to said mixing chamber at an angle less than a straight angle; said mixing chamber having an ambient air inlet aperture and said droplet disengaging chamber having an outlet port;

(b) an elongated manifold body mounted in said housing and extending transversely through said mixing chamber; said manifold body defining therewithin:

(1) a nebulizing chamber situated in a mid-region thereof, (2) a gas conducting channel extending from one end of said manifold body to said nebulizing chamber and communicating therewith, (3) a liquid conducting channel extending from the opposite end region of said manifold body to said nebulizing chamber, communicating therewith and the portion of said manifold body defining said liquid conducting channel terminating in a tapering nozzle for engaging a liquid source outlet and having a wedge-shaped annular protuberance that surrounds the tapering nozzle to provide a secondary seal about the liquid source outlet; and (4) aspirating means positioned in said nebulizing chamber and defining in combination with said nebulizing chamber:

(i) a gas passageway for conducting a pressurized gas stream from said gas conducting channel to a gas orifice which opens into said mixing chamber in a direction generally towards said disengaging chamber;

(ii) a liquid passageway for conducting a liquid stream from said liquid conducting channel to an annular opening located in said nebulizing chamber adjacent to said gas orifice and extending circumferentially thereabout; and (iii) an aerosol discharge orifice in substantial registry with said gas orifice and downstream therefrom; the interrelationship between said gas orifice and said annular opening being such that a pressurized gas stream issuing from said gas orifice entrains droplets of said liquid stream from said annular opening and disperses entrained droplets in said so issuing pressurized gas stream;

(c) a spray deflector means located in said mixing chamber and in the path of said so issuing gas stream from said aerosol discharge orifice, the relationship between the size of said spray deflector and the distance thereof from said aerosol discharge orifice being such that a major portion of liquid droplets emerging from said aerosol discharge orifice in such gas stream strike said spray deflector means, thereby breaking up said spray droplets into an aerosol which disperses into the issuing gas stream;

(d) gas connector means for connection of said gas conducting channel to a source of pressurized gas; and (e) liquid connector means for connection of said liquid conducting channel to said liquid source for the liquid to be nebulized and situated below said nebulizer device.

* * * * *